United States Patent [19]
Middleton

[11] 3,940,402
[45] Feb. 24, 1976

[54] TRIS(SUBSTITUTED AMINO) SULFONIUM SALTS

[75] Inventor: William Joseph Middleton, Chadds Ford, Pa.

[73] Assignee: E. I. DuPont de Nemours and Company, Wilmington, Del.

[22] Filed: Sept. 19, 1974

[21] Appl. No.: 507,426

[52] U.S. Cl. ....... 260/293.63; 260/80 C; 260/239 B; 260/293.51; 260/293.85; 260/326.61; 260/326.62; 260/326.82; 260/583 R; 260/583 EE
[51] Int. Cl.² ........................................ C07D 295/22
[58] Field of Search..... 260/293.63, 326.61, 326.62, 260/326.82, 583 EE, 293.85

[56] References Cited
UNITED STATES PATENTS 3,162,641   12/1964   Acker et al. .......................... 260/286

OTHER PUBLICATIONS

J.A.C.S. 84 : 3374–3387, (1962), Melby et al.

Primary Examiner—Sherman D. Winters
Attorney, Agent, or Firm—Anthony P. Mentis

[57] ABSTRACT

Trisaminosulfonium salts of the formula $(R^1R^2N)(R^3R^4N)(R^5R^6N)S^+ X^-$ wherein the R groups are alkyl of 1–20 carbons and each alkyl has at least 2 alpha hydrogens and X is selected from the group $(CH_3)_3SiF_2$, Cl, Br, I, CN, NCO, NCS $NO_2$ and $N_3$, are soluble in organic liquids. They are useful as polymerization catalysts and as reagents to replace other atoms or groups in organic compounds with F, Cl, Br, I, CN, NCO, NCS, $NO_2$ or $N_3$.

28 Claims, No Drawings

TRIS(SUBSTITUTED AMINO) SULFONIUM SALTS

BACKGROUND OF THE INVENTION

1. Field of the Invention

This invention relates to new tris(secondary amino) sulfonium salts that are useful, for example, as fluorinating agents and as polymerization catalysts.

2. Prior Art

No references to difluorotrimethylsilicic acid or any of its salts are known. One reference to a tris(dimethylamino)sulfonium salt is D. S. Acker & D. C. Blomstron, U.S. Pat. No. 3,162,641 (1964) to Du Pont. The preparation of tris-(dimethylamino)sulfonium tetracyano-quinodimethan (TCNQ) salt (TCNQide) by the reaction of lithium TCNQide with tris(dimethylamino)sulfonium fluoride is disclosed. The method of preparation or the properties of the fluoride are not disclosed.

DESCRIPTION OF THE INVENTION

Statement of Invention

This invention comprises a new class of organic soluble salts, their use as polymerization catalysts and as reagents for replacing atoms or groups in organic compounds with other atoms or groups, e.g. replacing other halogen atoms in organic compounds with fluorine atoms. These salts are trisaminosulfonium salts having the general formula

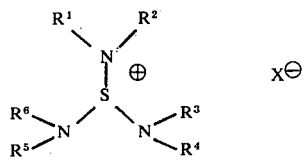

wherein
the R groups individually are alkyl of up to 20 carbon atoms each alkyl having at least two alpha-hydrogen atoms,
with the proviso that any or all of the pairs $R^1$ and $R^2$, $R^3$ and $R^4$ and $R^5$ and $R^6$ taken together form part of a 5- or 6-membered ring containing one nitrogen atom, any substituents being alkyl of up to 8 carbon atoms, and
X is selected from the group consisting of $(CH_3)_3SiF_2$, Cl, Br, I, CN, NCO, NCS, $NO_2$ and $N_3$.

The triaminosulfonium difluorotrimethylsilicates of the invention are prepared by treating a solution of sulfur tetrafluoride in an anhydrous inert solvent with at least three equivalents of a (secondary amino)trimethylsilane. The reaction appears to proceed in three steps:

1. In the first step, one equivalent of (secamino)-trimethylsilane reacts with sulfur tetrafluoride to give an aminosulfur trifluoride. This step can be conducted at a temperature range of from −100° to 0°.

2. In the second step, the produced aminosulfur trifluoride reacts with a second equivalent of (secamino)trimethylsilane to give a bis(amino)sulfur difluoride. This second step proceeds slowly at −80° but proceeds faster at a temperature of −30° to 0°.

3. In the third step, the bis(amino)sulfur difluoride reacts with a third equivalent of (sec-amino)trimethylsilane to give the final product, a tris(amino)sulfonium difluorotrimethylsilicate. This step proceeds at a temperature range of from 0° to 50°.

Each step can be conducted independently and each of the intermediates isolated or all three steps can be conducted in the same reaction vessel without isolation of the intermediates. Method "A" starts with step 1 and proceeds to the final product without isolation of the intermediate product whereas method "B" starts with step 2. The following equations illustrate the reaction.

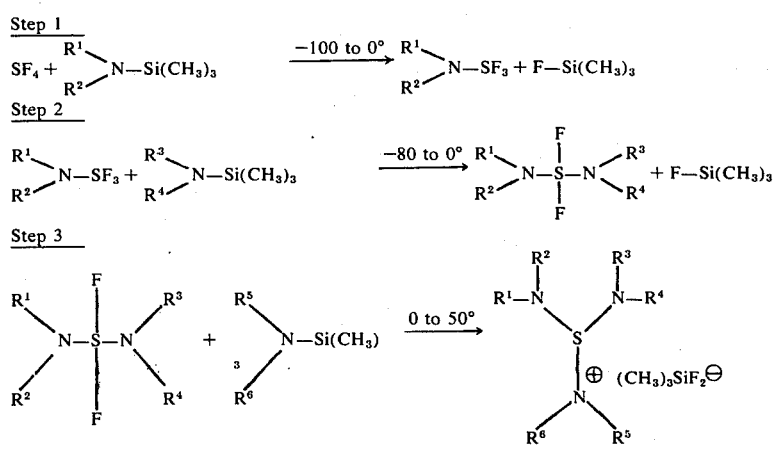

Salts where X is chloride are prepared by reacting a tris(secondary amino)sulfonium difluorotrimethylsilicate with a compound containing removable chlorine, as for example, α-chlorotoluene to obtain the sulfonium chloride salt as in Example 11 below. Reaction of the sulfonium chloride with appropriate reagents such as sodium cyanide, etc. will produce the sulfonium cyanide salt, etc. as illustrated below.

Solvents suitable for use in these reactions include ethers, such as diethyl ether, tetrahydrofuran and dimethylethylene glycol, and hydrocarbons such as pentane, hexane, toluene, and xylene. Halogenated hydrocarbons such as methylene chloride and chlorotrifluoromethane can be used in the first two steps but not in the third step. When all three steps are done in the same reaction vessel without isolation of intermediates, diethyl ether is the preferred solvent. Solvents containing active hydrogens must be avoided in all cases. Since water contains active hydrogen it is obvious the reactions must be carried out under anhydrous conditions.

Pressure is not critical. Ambient and/or autogenous pressure is the most convenient and therefore preferred.

The products and intermediates can be isolated and purified by conventional techniques such as distillation and recrystallization.

SPECIFIC EMBODIMENTS OF THE INVENTION

The following are illustrative examples in which all parts are by weight and all temperatures are in degrees Centigrade unless otherwise stated.

EXAMPLE 1

Tris(dimethylamino)sulfonium Difluorotrimethylsilicate

Method A $$3(CH_3)_2N-Si(CH_3)_3 + SF_4 \rightarrow [(CH_3)_2N]_3S^+(CH_3)_3SiF_2^- + 2(CH_3)_3SiF$$

A 152-g (1.3 mole) sample of dimethylaminotrimethylsilane was added dropwise to a solution of 22 ml (0.4 mole) of sulfur tetrafluoride in 400 ml of ether cooled to $-78°$. The reaction mixture was slowly warmed to room temperature and stirred for 3 days. The crystalline solid that precipitated was collected on a filter under dry nitrogen to give 109.0 g (99%) of tris(dimethylamino)sulfonium difluorotrimethylsilicate as colorless needles; mp 61°–67° (dec); $^{19}F$ nmr $(CD_3CN)$ $\delta$ $-60.3$ ppm (s); $^1H$ nmr $(CD_3CN)$ $\delta$ $-0.18$ ppm (s, 9H) and $+2.89$ ppm (s, 18H).

Anal. Calcd for $C_9H_{27}F_2N_3SSi$: C, 39.23; H, 9.88; F, 13.79; N, 15.25; S, 11.64; Si, 10.19. Found: C, 38.93; H, 10.17; F, 13.91; N, 15.31; S, 11.51; Si, 9.87.

EXAMPLE 2

Tris(dimethylamino)sulfonium Difluorotrimethylsilicate

Method B $$(CH_3)_2NSF_3 + 2(CH_3)_2NSi(CH_3)_3 \rightarrow [(CH_3)_2N]_3S^+ (CH_3)_3SiF_2^- + (CH_3)_3SiF$$

A solution of 20.4 g (0.174 mole) of (dimethylamino)trimethylsilane in 25 ml of ether was added dropwise to a solution of 10.65 g (0.08 mole) of (dimethylamino)sulfur trifluoride in 100 ml of ether cooled to $-50°$. The reaction mixture was slowly warmed to room temperature and stirred for 5 days. The white crystals that precipitated were collected on a filter under nitrogen, washed with ether, and dried under nitrogen. There was obtained 18.89 g (86%) of tris(-dimethylamino)sulfonium trimethyldifluorosilicate as colorless needles, mp 55°–72°, with nmr spectra identical to the sample prepared by Method A (Example 1).

EXAMPLE 3

Tris(pyrrolidino)sulfonium Difluorotrimethylsilicate $$3 \; \square N-Si(CH_3)_3 + SF_4 \longrightarrow (\square N-)_3 S^{\oplus} (CH_3)_3SiF_2^{\ominus} + 2FSi(CH_3)_3$$

A 47.3-g (0.33 mole) sample of pyrrolidinotrimethylsilane was added dropwise to a solution of 5.5 ml (ca. 0.1 mole) of $SF_4$ in 100 ml of ether cooled to $-78°$. The reaction mixture was slowly warmed to room temperature and then stirred overnight for 16 hours. The solid that precipitated was collected on a filter under nitrogen and dried in a vacuum desiccator over $P_2O_5$ to give 29.25 g of tris(pyrrolidino)sulfonium difluorotrimethylsilicate; mp 54°–57°; $^1H$ nmr $(CD_3CN)$ $\delta$ $-0.20$ ppm (s, 9H), 1.84 ppm (m, 12H), and 3.38 ppm (m, 12H); $^{19}F$ nmr $(CD_3CN)$ $\delta$ $-60.2$ ppm (s).

Anal. Calcd for $C_{15}H_{33}F_2N_3SSi$: C, 50.95; H, 9.41; F, 10.75; N, 11.88; S, 8.07; Si, 7.94. Found: C, 50.71; H, 9.58; F, 10.57; N, 12.01; S, 8.87; Si, 8.01.

EXAMPLE 4

Bis(dimethylamino)pyrrolidinosulfonium Difluorotrimethylsilicate $$\square N-SF_3 + 2(CH_3)_2NSi(CH_3)_3 \rightarrow$$

$$\square N-S^{\oplus} \begin{array}{c} N(CH_3)_2 \\ | \\ | \\ N(CH_3)_2 \end{array} (CH_3)_3SiF_2^{\ominus}$$

A 25.8-g (0.22 mole) sample of dimethylaminotrimethylsilane was added dropwise to a solution of 15.9 g (0.1 mole) of pyrrolidinosulfur trifluoride in 100 ml of ether cooled to $-60°$. The reaction mixture was warmed to room temperature and stirred for 3 days. Two liquid layers separated. The lower layer was separated, washed with ether, and the remaining materials were distilled off at reduced pressure (0.1 mm at 25°). The residue solidified to give 23.33 g of bis(dimethylamino)pyrrolidinosulfonium difluorotrimethylsilicate as a light yellow solid; mp 40°–45°; $^1H$ nmr $(CD_3CN)$ $\delta$ $-0.18$ ppm (s, 9H), 1.98 (m, 4H), 2.97 (s, 12H) and 3.20 (m, 4H); $^{19}F$ nmr $(CD_3CN)$ $\delta$ $-59.7$ ppm (s).

Anal. Calcd for $C_{11}H_{27}F_2N_3SSi$: C, 43.82; H, 9.69; F, 12.60; N, 13.94. Found: C, 43.52; H, 9.50; F, 12.50; N, 14.11.

EXAMPLE 5

Bis(pyrrolidino)(dimethylamino)sulfonium Difluorotrimethylsilicate $$(CH_3)_2NSF_3 + 2 \; \square N-Si(CH_3)_3 \longrightarrow$$

$$(\square N-)_2 S^{\oplus}-N(CH_3)_2 \; (CH_3)_3SiF_2^{\ominus} + F-Si(CH_3)_3$$

A solution of 13.3 g (0.1 mole) of dimethylaminosulfur trifluoride in 100 ml of ether was cooled to $-60°$, and 30.0 g (0.21 mole) of pyrrolidinotrimethylsilane was added dropwise. The reaction mixture was warmed to room temperature and stirred for 3 days. The lower liquid layer was separated, washed with ether, and the excess ether was removed by evaporation under reduced pressure to give 29.57 g (90%) of bis(pyrrolidino)(dimethylamino)sulfonium difluorotrimethylsilicate as a cream-colored solid; mp 49°–50°; $^1$H nmr (CD$_3$CN) δ −0.19 ppm (s, 9H), (m, 8H), 2.97 (s, 6H), 3.33 (m, 8H); $^{19}$F nmr (CD$_3$CN) δ −59.6 ppm.

Anal. Calcd for C$_{13}$H$_{31}$F$_2$N$_3$SSi: C, 47.67; H, 9.54; F, 11.60; N, 12.83. Found: C, 47.31; H, 9.77; F, 11.51; N, 12.50.

EXAMPLE 6

Tris(piperidino)sulfonium Difluorotrimethylsilicate

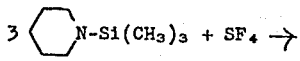

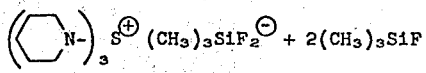

A solution of 2.75 ml (0.05 mole) of sulfur tetrafluoride in 50 ml of ether was cooled to −70°, and 26.7 g (0.17 mole) of piperidinotrimethylsilane was added dropwise. The reaction mixture was warmed to room temperature and stirred for 18 hours. The precipaited solids were collected on a filter (under nitrogen) and washed with ether to give 16.85 g (89%) of tris(-piperidino)-sulfonium difluorotrimethylsilicate as a white powder; mp 87°–90°; $^1$H nmr (CD$_3$CN) δ −0.17 ppm (s, 9H), 1.68 ppm (m, 18H) and 3.25 ppm (m, 12H); $^{19}$F nmr (CD$_3$CN) δ −59.8 ppm (s).

Anal. Calcd for C$_{18}$H$_{24}$F$_2$N$_3$SSi: C, 56.81; H, 6.36; F, 9.98; N, 11.04. Found: C, 56.47; H, 6.76; F, 10.11; N, 10.79.

EXAMPLE 7

Bis(dimethylamino)(diethylamino)sulfonium Difluorotrimethylsilicate (C$_2$H$_5$)$_2$NSF$_3$ + 2(CH$_3$)$_2$NSi(CH$_3$)$_3$ →

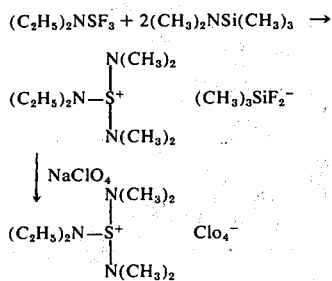

A solution of 25.8 g (0.22 mole) of dimethylaminotrimethylsilane was added dropwise to a stirred solution of 16.1 g (0.1 mole) of diethylaminosulfur trifluoride in 100 ml of ether cooled to −70°. The reaction mixture was warmed to room temperature and stirred for 1 week. Two liquid phases separated. The lower phase consisted primarily of bis(dimethylamino)(diethylamino)sulfonium difluorotrimethylsilicate. This phase was separated and mixed with a solution of 12.25 g (0.1 mole) of sodium perchlorate in 125 ml of water. The precipitate that formed was collected on a filter and recrystallized from alcohol to give 14.77 g (51%) of bis(dimethylamino)(diethylamino)sulfonium perchlorate as colorless, waxy crystals: mp 221°–223°; $^1$H nmr (DMSO-d$_6$) δ 1.18 ppm (t, J = 7Hz, 6H), 2.84 ppm (s, 12H), and 3.33 ppm (q, J = 7 Hz, 4H).

Anal. Calcd for C$_8$H$_{22}$ClN$_3$O$_4$S: C, 32.93; H, 7.60; Cl, 12.15; N, 14.40; S, 10.99. Found: C, 32.87; H, 7.60; Cl, 12.15; N, 14.37; S, 10.80.

EXAMPLE 8

Tris(N-methyl-N-octadecylamino)sulfonium Difluorotrimethylsilicate

2CH$_3$(CH$_2$)$_{17}$NHCH$_3$ + HN[Si(CH$_3$)$_3$]$_2$ →

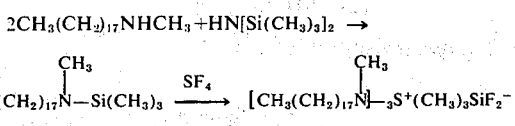

A mixture of 32.3 g (0.2 mole) of hexamethyldisilazane, 56.7 g (0.2 mole) of N-methyl-N-octadecylamine, and 0.2 g of ammonium chloride was refluxed for 2 days and then distilled to give 32.32 g of (N-methyl-N-octadecylamino)trimethylsilane as a colorless liquid, bp 168°–172° (0.8 mm), that solidified on cooling to a white solid, mp 35°–40°.

Anal. Calcd for C$_{22}$H$_{45}$NSi: C, 74.28; H, 13.88; N, 3.94. Found: C, 74.01; H, 13.78; N, 4.01.

A solution of 26.7 g (0.075 mole) of (N-methyl-N-octadecylamino)trimethylsilane in 25 ml of ether was added dropwise to a solution of 1.38 ml (0.025 mole) of sulfur tetrafluoride in 25 ml of ether cooled to −70°. The reaction mixture was warmed to room temperature and stirred for 3 days. The ether was removed by evaporation under reduced pressure to give 23.8 g (96% yield) of tris(N-methyl-N-octadecylamino)sulfonium difluorotrimethylsilicate as a waxy solid; mp 40°–60°; $^{19}$F nmr (CD$_3$CN) δ −59.6 ppm.

Anal. Calcd for C$_{60}$H$_{129}$F$_2$N$_2$SSi: C, 72.73; H, 13.12; N, 4.24; F, 3.84. Found: C, 72.59; H, 12.98; N, 4.11; F, 3.69.

EXAMPLE 9

Tris(4-methylpiperidino)sulfonium Difluorotrimethylsilicate

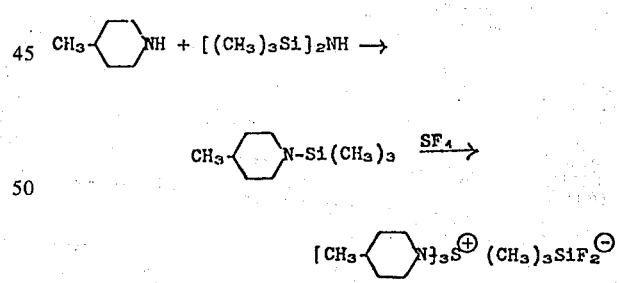

A solution of 80.7 g (0.5 mole) of hexamethyldisilazane, 99.18 g (1.0 mole) of 4-methylpiperidine, and 1 g of ammonium chloride was refluxed for 3 hours and then distilled to give a large amount of unreacted starting material and 31.05 g of (4-methylpiperidino)trimethylsilane as a colorless liquid: bp 83° (25mm).

Anal. Calcd for C$_9$H$_{21}$NSi: C, 63.08; H, 12.37; N, 8.17. Found: C, 62.89; H, 12.75; N, 8.09.

A 25.7-g (0.15 mole) sample of (4-methylpiperidino)trimethylsilane was added dropwise to a solution of 2.75 ml (0.05 mole) of sulfur tetrafluoride in 50 ml of ether cooled to −70°. The reaction mixture was warmed to room temperature and stirred for 2 days. Two liquid phases separated. The ether was removed by evaporation at reduced pressure to give 19.52 g (89%) of tris(4-methylpiperidino)sulfonium difluorotrimethylsilicate as an off-white solid: mp 73°–75°; $^{19}$F nmr (CD$_3$CN) δ −59.6 ppm; $^1$H nmr (CD$_3$CN) δ −0.18 ppm (s, 9H), 0.97 ppm (d, J = 5 Hz, 9H), δ 1.66 ppm (m, 15H) and δ 3.20 ppm (m, 12H).

Anal. Calcd for C$_{21}$H$_{45}$F$_2$N$_2$SSi: C, 57.62; H, 10.36; F, 8.68; N, 9.60. Found: C, 57.43; H, 10.11; F, 8.39; N, 9.31.

EXAMPLE 10

Tris(diethylamino)sulfonium Difluorotrimethylsilicate

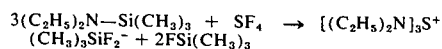

A solution of 85.7 g (0.59 mole) of diethylaminotrimethylsilane in 50 ml of ether was added dropwise to a solution of 10 ml (measured at −78°, 0.18 mole) of sulfur tetrafluoride in 200 ml of ether cooled to −70°. The reaction mixture was stirred for 3 days. Two liquid layers formed. The solvent and trimethylfluorosilane were removed by evaporation at reduced pressure to give 63.4 g (98% yield) of tris(diethylamino)sulfonium difluorotrimethylsilicate as light gray crystals: m.p. 90°–95°; $^1$H nmr (CD$_3$CN) δ −0.06 ppm (s, 9H), 1.23 ppm (t, 18H) and 3.33 ppm (q, 12H).

Anal. Calcd for C$_{15}$H$_{39}$F$_2$N$_3$SSi: C, 50.90; H, 10.93; F, 10.57; N, 11.68; S, 8.91. Found: C, 50.39; H, 11.20; F, 10.37; N, 11.71; S, 9.13.

Additional silicate compounds which can be prepared by using appropriate reactants in the disclosed reactions are shown in the following table.

EXAMPLE 12

Tris(dimethylamino)sulfonium Cyanide

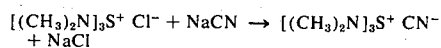

A solution of 60.6 g (0.3 mole) of tris(dimethylamino)sulfonium chloride in 250 ml methanol was mixed with a solution of 14.7 g (0.3 mole) of sodium cyanide in 100 ml methanol, and the sodium chloride that precipitated was filtered off. The filtrate was evaporated to dryness under reduced pressure, and the residue was recrystallized from acetonitrile-ether to give 53.0 g (93%) of tris(dimethylamino)sulfonium cyanide as colorless crystals: mp 214°–216°.

Anal. Calcd for C$_7$H$_{18}$N$_4$S: N, 29.44; S, 16.85. Found: N, 29.78; S, 16.61.

EXAMPLE 13

Tris(dimethylamino)sulfonium Thiocyanate

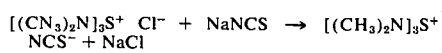

A solution of 20 g (0.1 mole) of tris(dimethylamino)sulfonium chloride in 10 ml of methanol was mixed with a solution of 8.1 g (0.1 mole) of sodium thiocyante in 40 ml of methanol. The sodium chloride that precipitated (6.97 g) was filtered off, and ether was added to the filtrate until no further precipitate formed. This precipitate was collected on a filter under nitrogen and dried to give 18.45 g of light yellow crystalline solid, mp 185°–190°. This solid was recrystallized to remove some remaining sodium chloride by dissolving in aceto-

TABLE I

| R$^1$ | R$^2$ | R$^3$ | R$^4$ | R$^5$ | R$^6$ | COMPOUND |
|---|---|---|---|---|---|---|
| ethyl | methyl | ethyl | methyl | ethyl | methyl | Tris(methylethylamino) sulfonium Difluorotrimethylsilicate |
| propyl | propyl | propyl | propyl | butyl | butyl | Bis(dipropylamino)(dibutylamino) sulfonium Difluorotrimethylsilicate |
| pentyl | pentyl | hexyl | ethyl | octyl | propyl | (dipentylamino)(hexyl-ethylamino)(octylpropylamino) sulfonium Difluorotrimethylsilicate |
| decyl | decyl | dodecyl | methyl | ethyl | eicosyl | (didecylamino)(dodecyl-methylamino)(ethyl-eicosylamino sulfonium difluorotrimethylsilicate |
| (4-octylpiperidine) | | methyl | methyl | methyl | methyl | (4-octylpiperidino)bis(dimethylamino) sulfonium difluorotrimethylsilicate |
| heptamethylene | | heptamethylene | | heptamethylene | | tris(azocino) sulfonium difluorotrimethylsilicate |
| 3-methyl-1,4-tetramethylene | | 3-methyl-1,4-tetramethylene | | 3-methyl-1,4-tetramethylene | | tris(3-methyl pyrrolidino) sulfonium difluorotrimethyl silicate |
| isobutyl | methyl | isobutyl | methyl | isobutyl | methyl | tris(isobutyl methylamino) sulfonium difluorotrimethylsilicate |
| neopentyl | methyl | neopentyl | methyl | neopentyl | methyl | tris(neopentyl methylamino) sulfonium difluorotrimethylsilicate |
| 3-ethylbutyl | methyl | methyl | methyl | methyl | methyl | (3-ethylbutyl methylamino)bis(dimethylamino) sulfonium difluorotrimethylsilicate |
| 3,5 dimethylheptyl | methyl | methyl | methyl | methyl | methyl | (3,5-dimethylheptyl methylamino)bis(dimethylamino) sulfonium difluorotrimethylsilicate |
| methyl | methyl | methyl | methyl | methyl | methyl | tris(dimethylamino) sulfonium difluorotrimethylsilicate |

EXAMPLE 11

Tris(dimethylamino)sulfonium Chloride

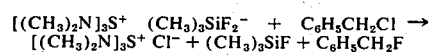

A solution of 88.6 g (0.32 mole) of tris(dimethylamino)sulfonium difluorotrimethylsilicate and 100 g α-chlorotoluene in 100 ml acetonitrile was stirred at 25° for 20 hours. Ether, 500 ml, was added and the solid that precipitated was collected under dry nitrogen on a filter and washed with ether. There was obtained 62.1 g (98% yield) of tris(dimethylamino)sufonium chloride as colorless crystals, mp 193°–194°.

Anal. Calcd for C$_6$H$_{18}$ClN$_3$S: N, 21.04; Cl, 17.73. Found: N, 20.96; Cl, 17.68.

nitrile, filteing, and reprecipitating by the addition of ether. There was obtained 15.76 g of tris(dimethylamino)sulfonium thiocyanate as colorless crystals, mp 185°–190°.

Anal. Calcd for C$_7$H$_{18}$N$_4$S$_2$: C, 37.81; H, 8.16; N, 25.20. Found: C, 37.59; H, 7.99; N, 25.62.

EXAMPLE 14

Tris(dimethylamino)sulfonium Nitrite

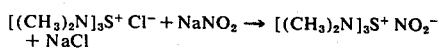

A solution of 20 g (0.1 mole of tris(dimethylamino)solfonium chloride in 10 ml methanol was mixed with a solution of 6.9 g (0.1 mole) of sodium nitrite in 350 ml methanol. Ether, 500 ml, was added to the clear reaction mixture, and the sodium chloride that precipitated was filtered off. The filtrate was evaporated to dryness under reduced pressure, and the residue was redissolved in 20 ml acetonitrile, filtered to remove some reamining sodium chloride, and then reprecipitated by adding 200 ml of dry ether. The precipitate was collected on a filter under nitrogen and dried in a vacuum desiccator over phosphorous pentoxide to give 19.06 g (91%) of tris(dimethylamino)sulfonium nitrite as colorless cyrstals, mp 156°–157° (decompose).

Anal. Calcd for $C_6H_{18}N_4O_2S$: C, 34.27; H, 8.63; N, 26.64; S, 15.25. Found: C, 34.11; H, 9.06; N, 26.42; S, 15.27.

EXAMPLE 15

Tris(dimethylamino)sulfonium Azide

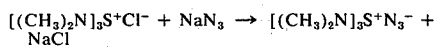

A mixture of 10 g (0.05 mole) of tris(dimethylamino)sulfonium chloride and 3.6 g (0.055 mole) of powdered sodium azide in 100 ml methanol was stirred at 25° for 3 days. Ether, 300 ml, was added, and the precipitated sodium chloride was filtered off. The filtrate was evaporated to dryness under reduced pressure and the residue (9.9 g, 96% yield) was redissolved in acetonitrile. This solution was filtered to remove a small amount of sodium chloride, and ether was added to the filtrate until no further precipitate formed. The precipitate was collected on a filter and washed with ether to give 8.9 g of tris(dimethylamino)sulfonium azide as a colorless, crystalline powder, m.p. 201°–206°(dec.).

Anal. Calcd for $C_6H_{18}N_6S$: C, 34.93; H, 8.79; N, 40.74; S, 15.54. Found: C, 35.11; H, 9.03; N, 40.51; S, 15.34.

EXAMPLE 16

Tris(dimethylamino)sulfonium Cyanate

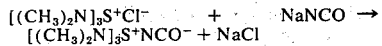

A mixture of 10 g (0.05 mole) of tris(dimethylamino)sulfonium chloride and 3.6 g (0.055 mole) powdered sodium cyanate in 100 ml methanol was stirred at room temperature (25°) for 3 days. Ether, 300 ml, was added, and the precipitated sodium chloride was filtered off. The filtrate was evaporated to dryness under reduced pressure and the residue was redissolved in acetonitrile, filtered, and then precipitated by the addition of ether. The precipitate was collected on a filter, washed with ether, and dried under dry nitrogen to give 9.27 g (90%) of tris(dimethylamino)sulfonium cyanate as a white crystalline powder, m.p. 202°–204°.

Anal. Calcd for $C_7H_{18}N_4OS$: C, 40.75; H, 8.79; N, 27.16; S, 15.54. Found: C, 40.58; H, 9.09; N, 27.30; S, 15.37.

The salts are colorless, crystalline solids that are very soluble in polar organic solvents. For example, three parts of tris(dimethylamino)sulfonium difluorotrimethylsilicate will dissolve in only one part of acetonitrile. In many reactions the difluorotrimethylsilicate anion behaves as though it is in equilibrium with fluoride ion and flurotrimethylsilane,

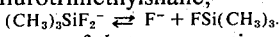

Because of these properties, these salts are useful as a source of organic soluble fluoride ion. Reactions that are catalyzed by fluoride ion can also be catalyzed by difluorotrimethylsilicate ion, and since the triaminosulfonium difluorotrimethylsilicates are soluble in a wide variety of organic solvents, these salts are more flexible catalysts than other fluoride ion sources such as potassium fluoride.

The salts are also useful in replacing Cl, Br, and I with F in organic compounds under very mild conditions. For example, the halogens of $C_2H_5I$, $C_6H_5CH_2Br$, $CHCl_3$ and $CH_2=CHCH_2Br$ are replaced quantitatively with F by reaction of the organic halide with the trimethylsilicate anion in acetonitrile at 25°. These halogen exchange reactions are many times faster than those normally effected with fluoride ion. For example, allyl bromide reacts with KF in polar organic solvents only at elevated temperatures (180°) but it will react with tris(dimethylamino)sulfonium difluorotrimethylsilicate at 25° to yield allyl fluoride. The fluorinated compounds prepared by these halogen exchange reactions are useful as propellants, refrigerants, and intermediates in the preparation of other fluorine-containing compounds which are difficult to obtain, including pharmaceuticals and herbicides, insecticides, and pesticides.

The tris(dialkylamino)sulfonium cyanide salts, where X in the general formula is CN, are useful in replacing Cl, Br, I or tosylate groups in organic compounds with CN groups under very mild conditions to prepare organic nitriles. The salts where X is NCO, NCS, $NO_2$ or $N_3$ are useful in preparing organic isocyanates, isothiocyanates, nitro compounds and azides respectively. The salts where X is Cl are useful in replacing sulfate or tosylate groups in organic compounds with Cl under very mild conditions. The salts where X is Br or I are useful in replacing Cl or tosylate groups with Br or I.

The following examples illustrate some of the utilities of the salts of the invention.

EXAMPLE A

Polymerization of Thiocarbonyl Fluoride with Tris(N-methyl-N-octadecylamino)sulfonium Difluorotrimethylsilicate as catalyst

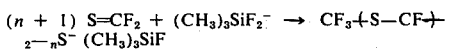

A 10-g sample of thiocarbonyl fluoride was slowly distilled into a stirred solution of 50 mg of tris(N-methyl-N-octadecylamino)sulfonium difluorotrimethylsilicate in 250 ml of pentane cooled to −78°. A white suspension of polymer formed immediately. The reaction mixture was stirred for 2 hours, and then warmed to 25°. The polymer was collected on a filter, washed with methanol, dilute nitric acid, and finally methanol again. It was then dried in a vacuum desiccator over phosphorus pentoxide and paraffin to give 9.5 g (95% yield) of white, rubbery poly-thiocarbonyl fluoride. A transparent, rubbery film was pressed from this polymer at 150° and 10,000 lb/sq in.

EXAMPLE B

Preparation of $CDCl_2F$ by Reaction of Tris(dimethylamino)sulfonium Difluorotrimethylsilicate with $CDCl_3$

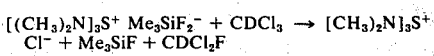

25-ml sample of $CDCl_3$ was injected into a flask containing 12.6 g (0.046 mole) of $(Me_2N)_3S^+Me_3SiF_2^-$, and the gases that evolved were condensed in a dry ice-cooled trap. The precipitate that formed in the reaction flask was collected on a filter under nitrogen, washed with ether, and dried under nitrogen to give 8.27 g (91%) of tris(dimethylamino)sulfonium chloride as a white crystalline hygroscopic powder, mp 193°–194°, $^1$H nmr (CD$_3$CN) δ 2.97 ppm (s).

Anal. Calcd for C$_6$H$_{18}$ClN$_3$S: C, 36.08; H, 9.08; Cl, 17.73; N, 21.04; S, 16.05. Found: C, 35.83; H, 9.38.

The condensate in the trap was distilled through a low temperature micro still to give 3.0 g of deuterodichlorofluoromethane, bp 9°–12°; $^{19}$F nmr (CCl$_3$F) δ −79.0 ppm (t, J$_{DF}$ = 13.0 Hz).

EXAMPLE C

Preparation of Benzyl Fluoride by Reaction of Tris(dimethylamino)sulfonium Difluorotrimethylsilicate with Benzyl Bromide

[(CH$_3$)$_2$N]$_3$S$^+$(CH$_3$)$_3$SiF$_2^-$ + φ—CH$_2$Br →
[(CH$_3$)$_2$N]$_3$S$^+$Br$^-$ + (CH$_3$)$_3$SiF + φ—CH$_2$F

Benzyl bromide, 342 mg (2 mmoles), was added to a solution of 275 mg (1 mmole) of (Me$_2$N)$_3$S$^+$Me$_3$SiF$_2^-$ in 1 ml of acetonitrile contained in an nmr tube. After one day the $^{19}$F nmr spectrum was determined. The spectrum indicated an equimolar amount of fluorotrimethylsilane (δ −152.8 ppm, 10-line multiplet, J = 7.5 Hz) and benzyl fluoride (δ −205.3 ppm; t, J = 47 Hz).

EXAMPLE D

Preparation of Allyl Fluoride by the Reaction of Tris(pyrrolidino)sulfonium Trimethyldifluorosilicate with Allyl Bromide

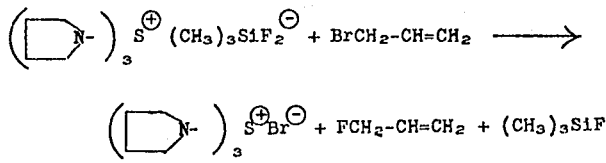

Allyl bromide, 4.4 ml (ca. 6.1 g, 0.05 mole), was added to a stirred solution of 7.1 g (0.02 mole) of tris(pyrrolidino)sulfonium trimethyldifluorosilicate in 5 ml of acetonitrile, and the reaction mixture was stirred for 2 hours at room temperature. The liquid portion was distilled off under reduced pressure to give a solid residue. Recrystallization from acetone-ether gave 5.0 g (78%) of tris(pyrrolidino)sulfonium bromide as colorless crystals; mp 85°–88°; $^1$H nmr (CD$_3$CN) δ 1.96 ppm (m, 12H) and δ 3.44 ppm (m, 12H).

Anal. Calcd for C$_{12}$H$_{24}$Br: C, 44.72; H, 7.51; N, 13.04. Found: C, 43.98; H, 7.59; N, 12.77.

The distillate was redistilled through a low temperature micro still to give 1.0 g (83%) of allyl fluoride as a colorless liquid, bp −3° to 0°; $^{19}$F nmr (CCl$_3$F) δ −216.7 ppm (t, d; J = 47, 14 Hz).

EXAMPLE E

Preparation of Ethyl Fluoride by Reaction of Tris(pyrrolidino)sulfonium Difluorotrimethylsilicate with Ethyl Iodide

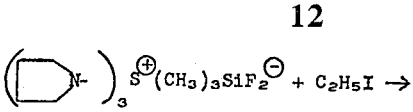

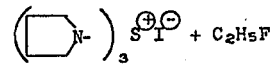

Ethyl iodide, 7.8 g (0.045 mole), was added to a solution of 7.1 g (0.02 mole) of tris(pyrrolidino)sulfonium difluorotrimethylsilicate in 5 ml of acetonitrile. The reaction mixture was evaporated to dryness and the residue was recrystallized from acetone-ether to give 5.2 g (70%) of tris(pyrrolidino)sulfonium iodide as colorless cyrstals; mp 100°–102°; $^1$H nmr (CD$_3$CN) δ 1.97 ppm (m, 12H) and δ 3.42 ppm (m, 12H).

Anal. Calcd for C$_{12}$H$_{24}$IN$_3$S: C, 39.03; H, 6.55; N, 11.38. Found: C, 38.88; H, 6.60; N, 11.30.

EXAMPLE F

Preparation of Ethyl Fluoride by Reaction of Bis(dimethylamino)pyrrolidinosulfonium Difluorotrimethylsilicate with Ethyl Iodide

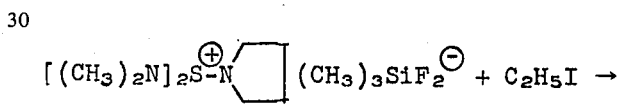

A 5.7-g (0.019 mole) sample of bis-dimethylamino)pyrrolidinosulfonium difluorotrimethylsilicate was dissolved in 5 ml of ethyl iodide. The gas that evolved was condensed in a dry ice-cooled trap and shown to be ethyl fluoride by $^{19}$F nmr. The solid that precipitated was collected in a filter, washed with ether, and recrystallized from alcohol/ether to give 3.95 g (66%) of bis(dimethylamino)pyrrolidinosulfonium iodide as colorless crystals; mp 175°–176.5°; $^1$H nmr (CD$_3$CN) δ 1.99 ppm (m, 4H), δ 3.00 ppm (s, 12H) and δ 3.24 ppm (m, 4H).

Anal. Calcd for C$_8$H$_{20}$IN$_3$S: C, 30.29; H, 6.35; N, 13.25. Found: C, 30.39; H, 6.40; N, 12.88.

EXAMPLE G

Preparation of Ethyl Fluoride from the Reaction of Bis(pyrrolidino)dimethylaminosulfonium Difluorotrimethylsilicate with Ethyl Iodide

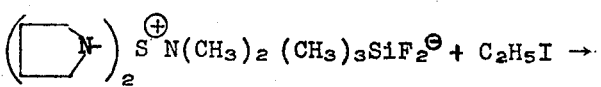

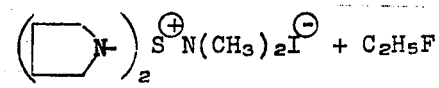

Ethyl iodide, 5 ml, was added to a solution of 9.8 g (0.03 mole) of bis(pyrrolidinol)dimethylaminosulfonium difluorotrimethylsilicate in 5 ml of acetonitrile. A gas (ethyl fluoride) was evolved. The reaction mixture was evaporated to dryness under reduced pressure, and the solid residue was broken up under ether and collected on a filter under nitrogen to give 8.97 g (95%) of bis(pyrrolidino)dimethylaminosulfonium iodide as a colorless hygroscopic solid: mp 52°–65°; $^1$H nmr (acetone-$d_6$) $\delta$ 2.06 ppm (m, 8H), $\delta$ 3.19 ppm (s, 6H) and $\delta$ 3.51 ppm (m, 8H).

Anal. Calcd for $C_{10}H_{22}IN_3S$: I, 36.97; Found: I, 37.02.

EXAMPLE H

Preparation of Ethyl Fluoride by Reaction of Trispiperidinosulfonium Difluorotrimethylsilicate with Ethyl Iodide

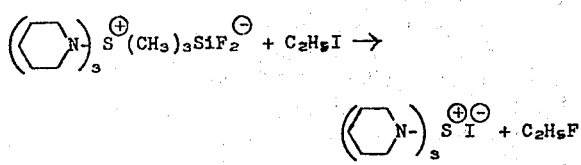

A solution of 7.6 g (0.02 mole) of tris(piperidino)sulfonium difluorotrimethylsilicate in 5 ml of ethyl iodide was allowed to remain at room temperature for 2 hours, during which time large crystals formed and gaseous ethyl fluoride was evolved. The crystals were collected on a filter and washed with ether to give 7.2 g of tris(piperidino)sulfonium iodide as colorless crystals, mp 176°–180°; $^1$H nmr (CD$_3$CN) $\delta$ 1.70 ppm (m, 18H) and $\delta$ 3.32 ppm (m, 12H).

Anal. Calcd. for $C_{15}H_{30}IN_3S$: C, 43.79; H, 7.37; N, 10.21. Found: C, 44.45; H, 7.47; N, 10.29.

EXAMPLE I

Preparation of Ethyl Fluoride by Reaction of Tris(dimethylamino)sulfonium Difluorotrimethylsilicate with Ethyl Iodide

[(CH$_3$)$_2$N]$_3$S$^⊕$(CH$_3$)$_3$SiF$_2^⊖$ + C$_2$H$_5$I →
[(CH$_3$)$_2$N]$_3$S$^⊕$I$^⊖$ + C$_2$H$_5$F + (CH$_3$)$_3$SiF

Ethyl Iodide, 3.14 g (0.02 mole), was mixed with a stirred solution of 5.5 g (0.02 mole) of (Me$_2$N)$_3$S$^+$Me$_3$SiF$_2^-$ in 5 ml of dry acetonitrile at 25°. The gas that evolved was condensed in a dry ice-cooled trap. The condensate in the trap was redistilled to give 1 ml of ethyl fluoride, bp −35° to −40° (identified by ir).

Ether, 50 ml, was added to the reaction mixture, and the white crystalline solid that precipitated was collected on a filter, washed with ether, and dried in air to give 5.37 g of tris(dimethylamino)sulfonium iodide salt as colorless crystals; mp 208–210°; $^1$H nmr (CD$_3$CN) $\delta$ 2.93 ppm (s).

Anal. Calcd for $C_6H_{18}IN_3S$: C, 24.41; H, 6.14; N, 14.23. Found: C, 24.70; H, 6.26; N, 14.29.

EXAMPLE J

Preparation of Benzyl Cyanide and Benzyl Isocyanide

The cyanide salt of Example 10 was reacted with α-bromotoluene as follows:

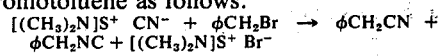

A 1.71-g (10 mmole) sample of α-bromotoluene was injected into a solution of 1.90 g (10 mmole) of tris(dimethylamino)sulfonium cyanide in 2.4 ml (1.9 g) acetonitrile, and the mixture was shaken. The mixture became warm. After cooling, analysis by gas chromatography showed that all of the α-bromotoluene had been consumed, benzyl cyanide was formed in 95% yield, and benzyl isocyanide was formed in 5% yield. Crystals of tris(dimethylamino)sulfonium bromide separated from the reaction mixture.

EXAMPLE K

Preparation of Heptanonitrile and Hexyl Isocyanide

The cyanide salt of Example 10 was reacted with 1-bromohexane as follows:

[(CH$_3$)$_2$N]$_3$S$^+$ CN$^-$ + CH$_3$(CH$_2$)$_5$Br →
CH$_3$(CH$_2$)$_5$CN + CH$_3$(CH$_2$)$_5$NC + [(CH$_3$)$_2$N]$_3$S$^+$Br$^-$

A 1.65-g (10 mmole) sample of 1-bromohexane was injected into a solution of 1.90 g (10 mmole) of tris(dimethylamino)sulfonium cyanide in 2.4 ml acetonitrile, and the mixture was shaken. The mixture became warm. Analysis by infrared and gas chromatography indicated that all of the 1-bromohexane was consumed, heptanonitrile ws formed in 94.5% yield, and hexyl isocyanide was formed in 4.5% yield.

EXAMPLE L

Preparation of Nonanitrile

The cyanide salt of Example 10 was reacted with 1-chlorooctane as follows:

[(CH$_3$)$_2$N]$_3$S$^+$ CN$^-$ + CH$_3$(CH$_2$)$_8$Cl →
CH$_3$(CH$_2$)$_8$CN

A 270-mg (2.5 mmole) sample of 1-chlorooctane was added to 5 ml of a 1M solution (5 mmole) of tris(dimethylamino)sulfonium cyanide in acetonitrile at 25°. The disappearance of the 1-chlorooctane and the production of nonanonitrile was followed by gas chromatographic analysis. The half-time of the reaction was 200 min.

For comparison, the above example was repeated with the sole exception that the cyanide salt of Example 10 was replaced with 5 mmole of tetraethylammonium cyanide, (C$_2$H$_5$)$_4$N$^+$ CN$^-$. The half time of the reaction was 540 minutes.

EXAMPLE M

Preparation of n-Hexyl Thiocyanate

The thiocyanate salt of Example 11 was reacted with 1-bromohexane as follows:

[(CH$_3$)$_2$N]$_3$S$^+$ SCN$^-$ + BrC$_6$H$_{13}$ → [(CH$_3$)$_2$N]$_3$S$^+$Br$^-$ + C$_6$H$_{13}$—SCN

A 7.4-g (0.45 mole) sample of 1-bromohexane was added at ambient temperature to a stirred solution of 11.1 g (0.05 mole) of tris(dimethylamino)sulfonium thiocyanate in 25 ml acetonitrile, and the rate of the reaction was followed by gas-liquid partition chromatography (glc). The reaction was one-half completed after 3 hr, and was essentially completed after 20 hr. The reaction mixture was poured into water and extracted with ether. The ether extract was dried (MgSO$_4$) and distilled to give 5.47 g (85%) of n-hexyl thiocyanate as a colorless liquid, bp 93°–94° (10 mm).

EXAMPLE N

Preparation of 1-Nitrohexane and 1-Hexyl Nitrite

The nitrite salt of Example 12 was reacted with 1-bromohexane as follows:

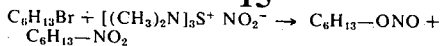

A 165-mg (1 mmole) sample of 1-bromohexane was added to 0.5 ml (1 mmole) of 2M tris(dimethylamino)-sulfonium nitrite in acetonitrile. The course of the reaction was followed by glc analysis. No further reaction occurred after 15 min. Glc analysis showed that 1-nitrohexane and 1-hexyl nitrite were formed in a 70:30 ratio.

EXAMPLE O

Preparation of Hexyl Azide

A 3.3 g (0.02 mole) sample of 1-bromohexane was added to a stirred solution of 5.15 g. (0.025 mole) of tris(trimethylamino)sulfonium azide in 15 ml acetonitrile at room temperature (25°). The course of the reaction was followed by glc analysis. One-half of the 1-bromohexane had reacted after 60 seconds, and the reaction was virtually complete after 15 min. Glc analysis of the crude reaction product indicated that hexyl azide was formed in 78% yield and 1-hexane was formed in 22% yield. The reaction mixture was poured into water (100 ml), and the organic portion that separated was taken up in ether, dried (MgSO$_4$) and distilled to give 1.9 g of hexyl azide as a colorless liquid, b.p. 53°–55°(0.5 mm).

EXAMPLE P

Preparation of 1-Hexyl Isocyanate

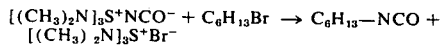

1-Bromohexane, 3.3 g (0.02 mole), was added to a stirred solution of 6.2 g (0.03 mole) of tris(dimethylamino)sulfonium cyanate in 12 ml of acetonitrile at 25°. The course of the reaction was followed by glc analysis. One-half of the 1-bromohexane had reacted after 6 min., and the reaction was virtually complete after 2 hours. Ether, 20 ml, was added to the reaction mixture to precipitate dissolved salts, and the reaction mixture was filtered. Distillation of the filtrate gave 2.16 g (85%) of 1-hexyl isocyanate as a colorless liquid, b.p. 50°–51° (10 mm).

I claim:

1. An anhydrous compound of the formula
   (R$^1$R$^2$N)(R$^3$R$^4$N)(R$^5$R$^6$N)S$^+$X$^-$
wherein the R groups individually are alkyl of up to 20 carbon atoms each alkyl having at least 2 alpha-hydrogen atoms, with the proviso that any or all of the pairs R$^1$ and R$^2$, R$^3$ and R$^4$ and R$^5$ and R$^6$ taken together with the nitrogen atom to which they are attached from a pyrrolidino or piperidino ring, any substituents being alkyl of up to 8 carbon atoms, and X is selected from the group consisting of (CH$_3$)$_3$SiF$_2$, Cl, Br, I, CN, NCO, NCS, NO$_2$ and N$_3$.

2. A compound of claim 1 wherein X is (CH$_3$)$_3$SiF$_2$.
3. A compound of claim 1 wherein X is Cl.
4. A compound of claim 1 wherein X is Br.
5. A compound of claim 1 wherein X is I.
6. A compound of claim 1 wherein X is CN.
7. A compound of claim 1 wherein X is NCO.
8. A compound of claim 1 wherein X is NCS.
9. A compound of claim 1 wherein X is NO$_2$.
10. A compound of claim 1 wherein X is N$_3$.
11. A compound of claim 2 where all the R groups are methyl; tris(dimethylamino)sulfonium difluorotrimethylsilicate.
12. A compound of claim 2 where all the R groups are part of a pyrrolidino ring; tris(pyrrolidino)sulfonium difluorotrimethylsilicate.
13. A compound of claim 2 where one pair of R groups are part of a pyrrolidino ring and the other R groups are methyl; bis(dimethylamino)pyrrolidinosulfonium difluorotrimethylsilicate.
14. A compound of claim 2 where two pairs of R groups are part of a pyrrolidino group and the remaining R groups are methyl; bis(pyrrolidino)(dimethylamino)sulfonium difluoromethylsilicate.
15. A compound of claim 2 where all the R groups are part of a piperidino ring; tris(piperidino)sulfonium difluorotrimethylsilicate.
16. A compound of claim 2 where one pair of R groups are ethyl and the others are methyl; bis(dimethylamino) (diethylamino)sulfonium difluorotrimethylsilicate.
17. A compound of claim 1 where each pair of R groups comprises a methyl group and an octadecyl group; tris)N-methyl-N-octadecylamino)sulfonium difluorotrimethylsilicate.
18. A compound of claim 1 where each pair of R groups are part of a 4-methylpiperidino ring; tris(4-methylpiperidino)sulfonium difluorotrimethylsilicate.
19. A compound of claim 1 where all the R groups are methyl and X is CN; tris(dimethylamino)sulfonium cyanide.
20. A compound of claim 1 where all the R groups are methyl and X is NCS tris(dimethylamino)sulfonium thiocyanate.
21. A compound of claim 1 where all the R groups are methyl and X is NO$_2$; tris(dimethylamino)sulfonium nitrite.
22. A compound of claim 1 where all the R groups are methyl and X is Cl; tris(dimethylamino)sulfonium chloride.
23. A compound of claim 1 where all the R groups are methyl and X is N$_3$; tris(dimethylamino)sulfonium azide.
24. A compound of claim 1 where all the R groups are methyl and X is NCO; tris(dimethylamino)sulfonium cyanate.
25. The process of making a compound of claim 1 where X$^-$ is (CH$_3$)$_3$SiF$_2$ comprising contacting at least 3 moles of

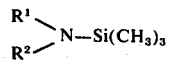

with 1 mole of SF$_4$ at a temperature range of −100° to 0°C. in the presence of a solvent having no ative hydrogen and recovering the compound.

26. The process of claim 25 in which diethyl ether is the solvent.
27. The process of making a compound of claim 1 where X$^-$ is (CH$_3$)$_3$SiF$_2$ comprising contacting (R$^1$R$^2$N)SF$_3$ with at least 2 moles of (R$^3$R$^4$N)Si(CH$_3$)$_3$ at a temperature range of −80° to 50°C. in the presence of a solvent having no active hydrogen and recovering the compound.
28. The process of making a compound of claim 1 where X$^-$ is (CH$_3$)$_3$SiF$_2$ comprising contacting equivalent amounts of (R$^1$R$^2$N)(R$^3$R$^4$N)SF$_2$ and (R$^5$R$^6$N)Si(CH$_3$)$_3$ at a temperature range of 0° to 50°C. in the presence of a solvent having no active hydrogen and recovering the compound.

* * * * *